US008551012B2

(12) United States Patent
Signorini et al.

(10) Patent No.: US 8,551,012 B2
(45) Date of Patent: Oct. 8, 2013

(54) METHOD FOR MONITORING ESTRUS AND OVULATION OF ANIMALS, AND FOR PLANNING A USEFUL FERTILIZATION TIME ZONE AND A PREFERRED FERTILIZATION TIME ZONE

(76) Inventors: Walter Signorini, Cremona (IT); Eleonora Rizzi, Annicco (IT)

( * ) Notice: Subject to any disclaimer, the term of this patent is extended or adjusted under 35 U.S.C. 154(b) by 536 days.

(21) Appl. No.: 12/877,688

(22) Filed: Sep. 8, 2010

(65) Prior Publication Data

US 2011/0218391 A1    Sep. 8, 2011

Related U.S. Application Data

(63) Continuation-in-part of application No. 11/940,125, filed on Nov. 14, 2007, now abandoned.

(30) Foreign Application Priority Data

May 25, 2007    (IT) .............................. MI2007A1072

(51) Int. Cl.
*A61B 10/00*    (2006.01)
*A61B 17/43*    (2006.01)
*A61D 19/00*    (2006.01)

(52) U.S. Cl.
USPC .............................. 600/551; 600/35; 119/174

(58) Field of Classification Search
USPC ..................................... 600/35, 551; 119/174
See application file for complete search history.

(56) References Cited

U.S. PATENT DOCUMENTS

| 3,876,767 | A | 4/1975 | Ose |
| 4,455,610 | A | 6/1984 | Rodrian |
| 7,083,575 | B1 | 8/2006 | Claycomb |
| 2003/0069515 | A1 | 4/2003 | Theelen et al. |
| 2005/0021295 | A1 | 1/2005 | Sasaguri |

FOREIGN PATENT DOCUMENTS

| GB | 2706259 | 12/1981 |
| NL | 1012872 | 2/2001 |
| WO | WO 2006/118508 | 11/2006 |

*Primary Examiner* — Rene Towa
*Assistant Examiner* — Emily Lloyd
(74) *Attorney, Agent, or Firm* — Adrian D. Battison; Ade & Company Inc.

(57) ABSTRACT

Estrus of animals and particularly sows is determined for planning of a preferred time period of insemination by a sensing system arranged to detect standing of the animal. Data from the sensing system is collected and analyzed using an algorithm and information that is displayed on an indicating system to provide an indication to a worker of the time period of estrus and ovulation and of a useful insemination time period and a preferred insemination time period of the animal. The indicating system includes a countdown clock to the preferred time period of insemination. In the event that the insemination fails, an indication is provided about whether the actual time of insemination occurred at the preferred time of insemination indicated to the worker. When estrus is completed, a confidence level is provided about the likelihood of success based on the position of the actual time of insemination relative to ovulation.

22 Claims, 10 Drawing Sheets

METHOD FOR MONITORING ESTRUS AND OVULATION OF ANIMALS, AND FOR PLANNING A USEFUL FERTILIZATION TIME ZONE AND A PREFERRED FERTILIZATION TIME ZONE

PRIOR APPLICATION INFORMATION

This application is a continuation in part of U.S. patent application Ser. No. 11/940,125 filed Nov. 14, 2007 now abandoned.

This invention relates to a method which is particularly designed for monitoring estrus and ovulation, and for planning a useful fertilization time zone and a preferred fertilization time zone; it can also be used to determine other physiological conditions such as illness or weakness in animals.

BACKGROUND OF THE INVENTION

The following description relates primarily to the monitoring of estrus and ovulation and the planning of a useful fertilization time zone and a preferred fertilization time zone in sows but can be applicable to other animals.

Nowadays is known the strict relation that exists between the estrus and ovulation status, and the following features of the animal: blood temperature, vulva appearance and state of stress in presence of the boar.

On the basis of this relation, a typical method for the determination of the estrus and ovulation status of the sow consists in the evaluation by an expert staff, through direct observation of the animals, of at least one of the characteristics mentioned above.

In U.S. Pat. No. (Rodrian) 4,455,610 Jun. 19, 1984 is disclosed a tag carrying a mercury switch which can be attached to the animal to detect movement. Information relating to the amount of movement is used in a complicated system that detects estrus of the animal by comparing rates of movement.

In Published European Patent Application EP 1 200 119 A2 (Theelen) published Sep. 4, 2003 which corresponds to U.S. Published Application 2003/0069515 (now abandoned) is disclosed a complicated system that detects estrus of the sow by detecting standing movements by a sensor above the animal in response to stimulation by a boar or a simulated boar. Different steps of the estrus are detected by different responses to stimulation.

In UK Patent Application 2 076 259 (Rodrian) published Nov. 25, 1981 is disclosed a similar arrangement which is primarily concerned with a transceiver unit for receiving information from the transponder on the animal.

NL Patent Application 1012872 published Feb. 23, 2001 discloses a device for measuring animal lying time for detection of estrus In order to improve the effectiveness of fertilization it is necessary to detect the estrus properly, because the useful interval for the sow fertilization starts from the peak of heat. Thus it is necessary to detect when the heat starts and when the heat reaches a peak, otherwise the fertilization may fail. This requires conventionally the necessity for frequent inspections of the animals.

The technician also knows the fact that the fertilization has more probability to be effective if performed in a particular period of the estrus, so an inadequate survey of the estrus of a sow has as an effect and high probability of failure of fertilization, with a severe reduction for the sow productivity, which enters on estrus every 21 days.

Any failures thus significantly increase costs, of maintaining and feeding the animal during the time when it is non-productive. Also any repeated fertilization attempts to safeguard against failures significantly increase costs of semen and labor.

The conventional methods present some difficulties, for example the requirement for qualified staff dedicated to frequent inspections of every sow, and even in this situation fertilization is subject to the variability and possibility to failure which arises from the strong dependence upon the "human factor".

SUMMARY OF THE INVENTION

It is one object of the present invention to provide a method to monitor estrus and ovulation and plan a useful fertilization time zone and a preferred fertilization time zone; it can also be used to determine other physiological conditions such as illness or weakness in animals where the method can provide a number of different features important in monitoring the animal.

According to a first aspect of the invention there is provided a method to plan a useful fertilization time zone and a preferred fertilization time zone of an animal comprising:

providing a sensing system arranged relative to an animal so as to detect standing of the animal;

collecting data from the sensing system;

wherein the data comprises data relating to the total time during which the animal is standing within a predetermined time period;

and analyzing the data using an algorithm to determine a time zone of ovulation of the animal;

and providing an indicating system to provide an indication to a worker of the time zone of ovulation.

The time zone of ovulation, which is determined in this method, is that part of the estrus where ovulation is occurring or is believed to be occurring so that fertilization can be best performed with the best probability of success.

Preferably the algorithm is arranged to detect changes in the standing time.

Preferably, when the changes are first detected indicative of estrus, the algorithm is arranged to calculate from those changes a start time of the changes. This is done by interpolation of the data to work back from the time that the changes are detected to the actual start time of those changes. Once start time of estrus is established, the system will predict a useful time zone of fertilization.

Also preferably the algorithm is arranged to calculate from the changes a peak in the changes and to establish the time zone of ovulation, and confirm a preferred time of fertilization from the calculated start time and the calculated peak of the changes.

Preferably the indicating system is arranged to provide a first indication to the worker when a change is detected indicative of estrus and of a useful fertilization time zone, and a second indication indicative of a preferred time of fertilization within the period of ovulation. These indications can be of many forms including a light and a time display on the sensing system, a graph display on a central computer screen, or on a hand held display such as a PDA, or all of these.

Preferably, in addition, the indicating system is arranged to provide to the worker a countdown indication of time to the preferred time zone of fertilization. This is preferably performed by a countdown digital clock although other displays such as bar graphics can be used.

Preferably the indicating system is arranged to provide an indication indicative of a preferred time of fertilization within the time zone of ovulation and wherein there is provided an input indicative of an actual time of fertilization, and the method is arranged to provide an indication about whether the actual time of fertilization occurred at the indicated preferred time of fertilization within the time zone of ovulation, and to confirm by means of a color graph the level of confidence of the results of fertilization. This is particularly useful to monitor the accuracy of the worker's activities to ensure that the system is properly followed by the worker to maintain a best efficiency of fertilization.

Preferably the data is analyzed by using the algorithm to determine an estrus and a useful fertilization time zone of the animal. This is for example the estrus after a weaning. However it can also apply to gilts which have or have not had a previous estrus, or to gestating sows that for some reasons such as sickness or miscarriage, may experience heat returns. In relation to the sow after weaning, the sow may sometimes be moved after weaning to a new location and this can lead to a period of stress. Thus the algorithm is preferably arranged to discount a period of stress of the animal prior to estrus since this stress can also cause increased standing time which can interfere with the analysis of the standing time to determine estrus and a useful fertilization time zone.

Preferably the method includes providing an input to be actuated by the worker indicative of an actual time of fertilization and, when estrus is completed, the method uses the algorithm to provide a calculation of a confidence level about the position of the actual time of fertilization relative to the time zone of ovulation. In this way after the process is completed and the situation is reviewed, bearing in mind all the data from the estrus period, the system indicates by means of a color graph, how successful the fertilization is likely to be, allowing the future handling of the animal to be better planned.

In accordance with an important feature, in the event that a preferred time of fertilization within the ovulation time zone is outside a scheduled work period of the worker, the method includes indicating means to communicate to the worker an alternative time within a scheduled work period. This allows the worker to plan his schedule bearing in mind all the other tasks to be performed to carry out the fertilization at a convenient time while maintaining the best probability of success relative to the ovulation time zone.

Preferably there is provided an input indicative of an actual time of fertilization and wherein the indicating system is arranged to provide a first signal when a change is detected indicative of estrus and of a useful fertilization time zone, a second signal indicative of peak of estrus, a third signal indicative of commencement of the time of ovulation and of a preferred fertilization zone, a fourth signal indicative of alternative fertilization time for out of work shift applications, a fifth signal indicative of completion and registration of fertilization, and a sixth signal indicative of illness or weakness of animals These signals are preferably readily visible by the worker at the location of the animals so that the worker can notice easily the useful fertilization time zone, the preferred fertilization time zone, and illness or weakness status of the animals, bearing in mind that the worker may be managing a herd of hundreds of animals coming into the estrus cycle.

As an alternative possible feature the method includes supplying feed and water to the animal and providing a signal indicative to the worker if, after supply of the feed and/or water, the animal does not stand which is an indication of illness or weakness of the animal leading to a requirement for intervention either by the worker or the veterinarian.

Fertilization can be carried out in all cases by artificial means or by other means including the natural servicing of the animal by a male.

While the methods described herein are primarily concerned with the raising of hogs and the management of sows, the invention is not so limited and other animals such as cows or some others may be contemplated.

According to a second aspect of the invention there is provided a method to plan a useful fertilization time zone and a preferred fertilization time zone of an animal comprising:
providing a sensing system arranged relative to an animal so as to detect a changing characteristic of the animal indicative of estrus and useful fertilization time zone of the animal;
collecting data from the sensing system;
analyzing the data using an algorithm to determine a time zone of ovulation of the animal and a preferred time of fertilization within the time zone of ovulation;
and providing an indicating system to a worker;
wherein the indicating system is arranged to provide to the worker a countdown indication of time to the preferred time zone of fertilization.

According to a third aspect of the invention there is provided a method to plan a useful fertilization time zone and a preferred fertilization time zone of an animal comprising:
providing a sensing system arranged relative to an animal so as to detect a changing characteristic of the animal indicative of estrus and useful fertilization time zone of the animal;
collecting data from the sensing system;
analyzing the data using an algorithm to determine a time zone of ovulation of the animal and a preferred time of fertilization within the time zone of ovulation;
providing an indicating system to a worker for indicating the preferred time of fertilization within the time zone of ovulation;
providing an input indicative of an actual time of fertilization;
and, in the event that the fertilization fails, providing an indication about whether the actual time of fertilization occurred at the preferred time of fertilization indicated to the worker.

According to a fourth aspect of the invention there is provided a method to plan a useful fertilization time zone and a preferred fertilization time of an animal comprising:
providing a sensing system arranged relative to an animal so as to detect a changing characteristic of the animal indicative of estrus and useful fertilization time zone of the animal;
collecting data from the sensing system;
analyzing the data using an algorithm to determine a time zone of ovulation of the animal;
providing an input indicative of an actual time of fertilization;
and when estrus is completed, using the algorithm to provide a calculation of a confidence level about the position of the actual time of fertilization relative to ovulation.

According to a fifth aspect of the invention there is provided a method to plan a useful fertilization time zone and a preferred fertilization time of an animal comprising:
providing a sensing system arranged relative to an animal so as to detect a changing characteristic of the animal indicative of estrus and useful fertilization time zone of the animal;
collecting data from the sensing system;
analyzing the data using an algorithm to determine a time zone of ovulation of the animal and a preferred time of fertilization within the time zone of ovulation;
providing an indicating system to a worker for indicating the preferred time of fertilization within the time zone of ovulation;
wherein, in the event that a preferred time of fertilization within the ovulation time zone is outside a scheduled work period, communicating to the worker an alternative time within a scheduled work period.

The method described hereinafter for the monitoring of the estrus and ovulation, and for planning a useful fertilization time zone and a preferred fertilization time zone of sows or other animals provides a central unit connected to a plurality of detector devices which are linked to a respective sow and suitable to determine a standing status of the sow and the time spent by the sow in such status. The central unit includes means of data capture detected by detector devices and is able to determine the beginning of the estrus status and a useful fertilization time zone of the sow, so to suggest the preferred period of time within the time of ovulation for the fertilization to be carried out. In a particular example of the algorithm, the processor can perform a moving integration of data and calculating two moving averages, one fast and the other slow, of the moving integral. A positive difference between the fast moving average and the slow one, together with the survey of a state of nocturnal anxiety of the sow higher than a certain threshold, is used to determine the beginning of the estrus and useful fertilization time zone.

The task of the method described is to realise an instrument for the automatic determination of the estrus and ovulation peak status of the sow with a very low delay compared with the instant during which the estrus status has effectively begun.

In the field of such a task, a purpose of the method described is to provide a method for the determination of the physiological status of the sow, effective in the determination of estrus and useful fertilization time zone, and ovulation and a preferred fertilization time zone following the weaning of the sows, or in the determination of estrus and a useful fertilization time zone and ovulation and a preferred fertilization time zone of gilts, or in the determination of estrus and a useful fertilization time zone and ovulation and a preferred fertilization time zone of gestating sows that experience heat returns due to illness or miscarriage.

The algorithm is arranged to effect determination of the estrus and ovulation status of the sow relative to the stress status of the sow, sampled during all hours of the day and the night.

The algorithm is arranged to provide automatic determination of the estrus and a useful fertilization time zone and ovulation peak and a preferred fertilization time zone of the sow with much less delay in regard to the moment when the state of heat has effectively commenced.

In the method described, a central unit is connected to at least one detector device, which can be associated with a corresponding sow and is able to determine a state of standing of the sow and the time spent by the sow in this state. The method further includes collating in a processor data detected by the detector device; calculating a moving integral of the times of erect posture, acquired at a constant rate by said at least one detector device, said moving integral being calculated over a first interval of time; calculating a short moving average of said moving integral over a second interval of time, less than the first interval of time; calculating a long moving average of the moving integral over a third interval of time greater than the second interval of time and less than the first interval of time; determining the onset of the state of heat of the sow and a useful fertilization time zone to send a signal for the onset of the state of heat when the short moving average is greater than the long moving average for at least a predetermined time interval.

The algorithm can estimate within the estrus zone the ovulation zone and estimate within the ovulation zone a preferred time for fertilization, able to estimate the time frame in which the sow should be fertilized based upon the distance between the end of weaning and the detected onset of the state of heat.

Furthermore, the algorithm can effect scheduling of a preferred time zone of fertilization, by verifying that the short moving average remains less than the long moving average for at least a predetermined interval of time and, if so, to determine the preferred time of fertilization as the fraction of time elapsed between the time of onset of the state of heat and the time when the short moving average becomes less than the long moving average.

BRIEF DESCRIPTION OF THE DRAWINGS

Further characteristics and advantages of the device will mainly result from the description of a preferred execution form, but not exclusive, of the device according to the device, illustrated, with an indicative and not limitative intent, in the attached drawings where.

DETAILED DESCRIPTION

Definitions

Figure 1:
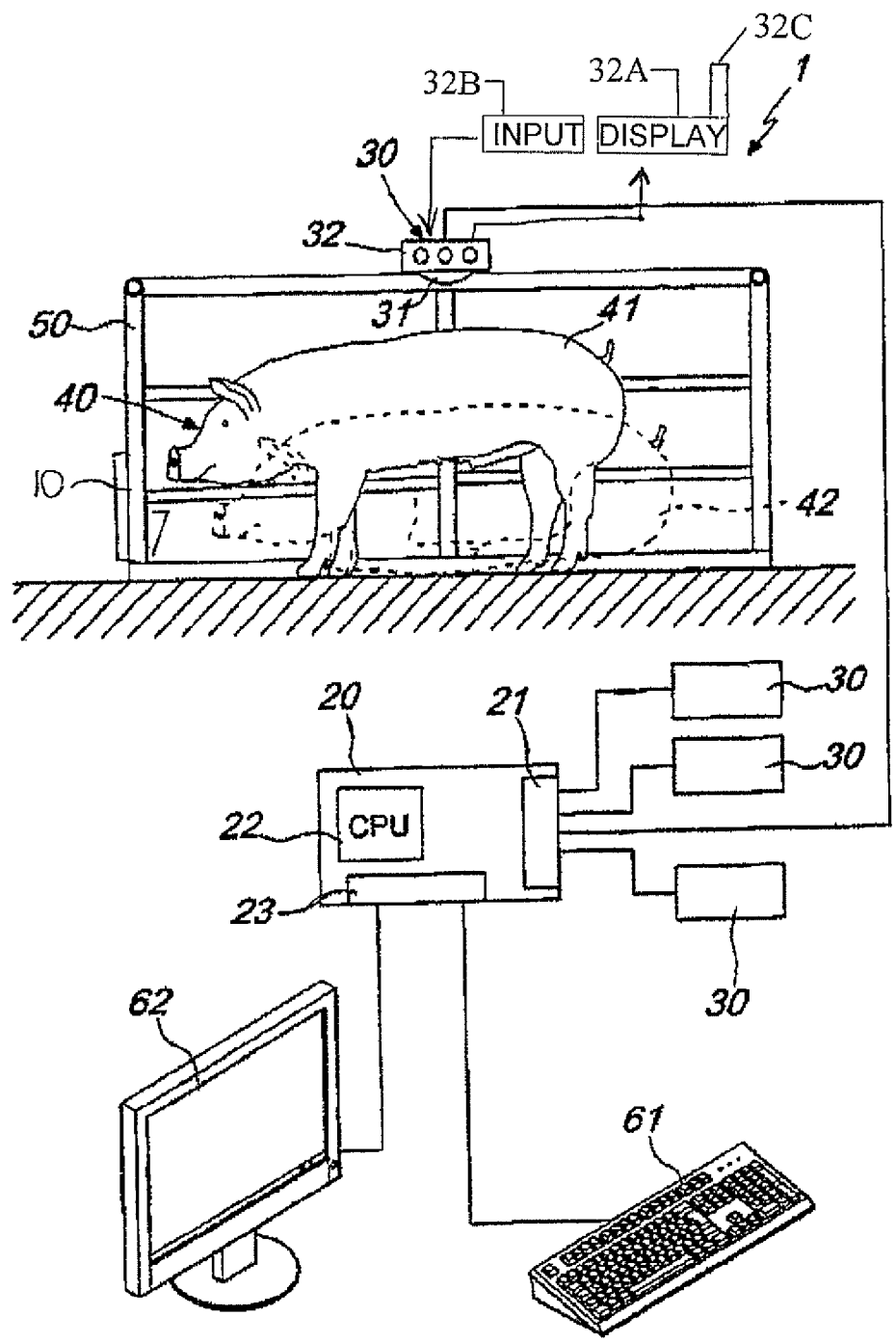
FIG. 1 illustrates a diagram of the apparatus according to the invention.

| Name | Description |
| --- | --- |
| ACTS | Actual Time Stamp |
| CB | Curve Blue |
| CO | Curve Orange |
| CP | Curve Pink |
| CBact | Curve Blue Actual value |
| CPact | Curve Pink Actual value |
| CBmin | Curve Blue minimum Value |
| CBMax | Curve Blue maximum Value |
| AVCPx | Average of CP in the day x after weaning |
| PAP | Pre Analysis Period |
| HS | Heat Start |
| HSTS | Heat Start Time Stamp |
| CBMaxAfterHS | CBMax After HSTS |
| CBDeltaMax | Max Range Of CB Before Heat Peak |
| AHSD | Average Heat Semi Duration |
| WTS | Weaning Time Stamp |
| PITS | Provisional Fertilization Time Stamp |
| mHD | Minimum Heat Duration |
| MHD | Maximum Heat Duration |
| UIZ | Useful Zone For Fertilization |
| UIZB | Useful Zone For Fertilization Begin |
| UIZE | Useful Zone For Fertilization End |
| DBHP&OTZB | Delay Between Heat Peak And Ovulation Time Zone Begin |
| OZB | Ovulation Zone Begin |
| OZE | Ovulation Zone End |
| SmD | Semen Minimum Duration |
| OmV | Ovules Minimum Vitality |
| HP | Heat Peak |
| HPTS | Heat Peak Time Stamp |
| AID | Artificial Fertilization Done |
| BLHS | Bezel LED Heat Signal |
| BLIS | Bezel LED Fertilization Signal |
| TLHS | Top Light Heat Signal |
| TLIS | Top Light Fertilization Signal (confirmed) |
| SSE | Sow Substitution Event |
| GIT | Graph Intensity Type |
| NMT | Night Movement Type |
| MTI | Movement Type Indicator |
| TPK | Type Of Peak 0 In The Day, 1 In the Night |

Evaluation of the Raw Data

The time the sow is Up is taken by the device every 10 minutes, defined by the variable tup. This is the raw data coming from the sow. Every hour the device computes this data:

$$Tup_i = \sum_1^6 tup$$

Where "i" is the actual hour.

After this the device computes the new point on the graph using this procedure:

Step 1: Computing of the Moving Integral

The moving integral is given by the following equation:

$$MovInt_t = \int_{t-24}^{t} Tup * dt$$

Where t is the actual hour. Therefore every hour this value is computed using the last 24 hours and disregarding the oldest 25$^{th}$ hour.

dt is the is the time interval used for the evaluation, that is one hour. This is the reason why every hour the device is able to plot a new point onto the graph. The device gets a Time Up acquisition every 10 minutes, therefore the software adds together 6 consecutive acquisitions, before running a new integral evaluation.

Step 2: Computing of the Moving Integral for Night Activities

The moving integral for the night activities is given by the following equation:

$$MovIntNight_t = \int_{t-24}^{t} Tup_n * dt$$

Where t is the actual hour, n are the hours in the night period (from 9 pm till 6 am) that means that all the data of Tup for the daily period from 7 am till 8 pm are not taken in account. Therefore every hour this value is computed using the last 24 hours and disregarding the oldest 25$^{th}$ hour.

dt is the time interval used for the evaluation, that is one hour.

Step 3: Computing of the Blue Curve (CB)

The moving integral is not plotted, but it is the input of two moving averaging processes using two periods: 12 hours and 7 hours: That is to say a long moving average and a short moving average. "dt" is the time interval of one hour. The short moving average is plotted in the above graph as a blue curve, the long moving average is plotted as an orange curve.

Every point of the Blue curve of the graph is the result of this computation:

$$CB_t = \sum_{t-7}^{t} MovInt_t / 7$$

Where t is the actual hour. Therefore every hour this value is computed using the last 7 values of the moving integral.

For example at 10 pm of the 2$^{nd}$ of December the Y value is given by this equation:

$$CB_{10pm-2/10} = \sum_{3pm}^{10pm} MovInt_t / 7$$

Step 4: Computing of the Orange Curve (CO)

Every point of the Orange curve of the graph is the result of this computation:

$$CO_t = \sum_{t-12}^{t} MovInt_t / 12$$

Where t is the actual hour. Therefore every hour this value is computed using the last 12 values of the moving integral.

For example at 10 pm of the 2$^{nd}$ of December (indicated by the arrow in the graph) the Y value is given by this equation:

$$CO_{10pm-2/10} = \sum_{10am}^{10pm} MovInt_t / 12$$

These two different moving average curves are useful to check if the Blue Curve has a positive trend or negative, because it is sufficient to check the Y value of the two curves at the same time, if the Blue Y value is greater than the Orange one, the Blue curve has a positive trend, otherwise it has a negative trend. This is also very useful to check the peak in the estrus graph with Gaussian shape, because in this case the device looks for a sequence such as positive, null, negative trend.

Step 5: Computing of the Pink Curve (CP)

Every point of the Pink curve of the graph is the result of this computation:

$$CP_t = \sum_{t-12}^{t} MovIntNight_t / 12$$

Evaluation During PAP (Pre-Analysis Period)

During the first two days after the sow has been moved into the stall (just after the weaning) the device computes the following value that will be used to classify the resulting graph of the sow:

CBMV and CBMV-Time Stamp that means the maximum value of CB in the first 1, 5 days after the weaning and its Time Stamp.

AVCP1, that means the average of CP value computed at a time around noon, that is, from 10 am till 2 pm in the first day after weaning.

AvCP2, that means the average of CP value computed at a time around noon from 10 am till 2 pm in the second day after weaning.

Classification of Graph for Intensity

This procedure allows the Algorithm to classify in 3 types of graphs in terms of percentage of sow activity during the PAP period. This classification is called GIT (Graph Intensity Type) and it will be used in the computation of the parameter MTI (Movement Type Indicator)

| | |
|---|---|
| If CBMV < 10% | GIT=0 |
| If 10 <= CBMV < 20% | GIT=1 |
| If CBMV >= 20% | GIT=2 |

Classification of Night Behavior

This procedure allows the Algorithm to classify into 3 different categories the night sow activities in the PAP period. This classification is called NMT (Night Movement Type) and it will be used in the computation of the parameter MTI (Movement Type Indicator).

| | |
|---|---|
| If Max[AVCP1, AVCP2] < 3% | NMT=0 |
| if CBMV-CBMV/3 <= Max[AVCP1, AVCP2] | NMT=2 |
| Otherwise | NMT=1 |

Computation of Movement Type Indicator MTI

It is given by this simple combination of GIT & NMT parameters.

| MTI | GIT | NMT | Description |
|---|---|---|---|
| 0 | 0 | 0 | Very low activity during the day and night |
| 1 | 0 | 1 | Very low activity during the day, low activity during the night |
| 2 | 0 | 2 | Very low activity during the day, significant activity during the night |
| 3 | 1 | 0 | Significant movement during the day, Very low movements during night |
| 4 | 1 | 1 | Significant activity during the day and night |
| 5 | 1 | 2 | Significant activity during the day, high activity during the night |
| 6 | 2 | 0 | High activity during the day, very low activity during the night |
| 7 | 2 | 1 | High activity during the day, significant activity during the night |
| 8 | 2 | 2 | High activity during the day, and night |

Trend Classification

This classification comes from the values AVCP1 and AVCP2. This allows the exclusion of impossible areas where the HS will be, and to classify the graph into 26 different types. This indicator is called TT2 (Trend Type at $2^{nd}$ day).

| | |
|---|---|
| If (AVCP1 >= 1.2*AVCP2) and NMT>0 | TT2=1 /* CP Trend is trailing*/ |
| else if (AVCP2 >= 1.2*AVCP1) and NMT>0 | TT2=2 /* CP Trend is leading */ |
| Otherwise TT2=0 | /*Trend Flat */ |

Graph Final Classification

It is given by this simple combination of MTI & TT2 parameters.

For all these different GITs the algorithm may use different strategies to determine these main important events:

If the heat starts during the night or the day

The HSTS

If the heat may start from the $2^{nd}$ day or not

| GIT | MTI | TT2 |
|---|---|---|
| 0 | 0 | 0 |
| 1 | 1 | 0 |
| 2 | 2 | 0 |
| 3 | 3 | 0 |
| 4 | 4 | 0 |
| 5 | 5 | 0 |
| 6 | 6 | 0 |
| 7 | 7 | 0 |
| 8 | 8 | 0 |
| 9 | 0 | 1 |
| 10 | 1 | 1 |
| 11 | 2 | 1 |
| 12 | 3 | 1 |
| 13 | 4 | 1 |
| 14 | 5 | 1 |
| 15 | 6 | 1 |
| 16 | 7 | 1 |
| 17 | 8 | 1 |
| 18 | 0 | 2 |
| 19 | 1 | 2 |
| 20 | 2 | 2 |
| 21 | 3 | 2 |
| 22 | 4 | 2 |
| 23 | 5 | 2 |
| 24 | 6 | 2 |
| 25 | 7 | 2 |
| 26 | 8 | 2 |

For every GIT the algorithm uses control parameters that must be satisfied before being able to say that there is a heat. These parameters are expressed in percentage, in this way we do not have a fixed threshold but only a relative one. The parameters are:

| | |
|---|---|
| % CBmin | (ΔCB relative) |
| % CBDelta | (ΔCB absolute) |
| % CPPrev | (ΔCP relative) |
| % CPDelta | (ΔCP absolute) |
| CBMPV | |

Computation of CBmin and CBref

The search for CBmin, may start from 2 pm of the second day for each sow. For all the graphs this value could also be good for CBref if the Heat starts in the 3rd day. Otherwise the algorithm has to look for another CBmin in the day just before a leading trend of AVCPx. This CBmin will be the value for CBref and this will be the best one for the computation of % CBmin.

FIG. 1 shows an apparatus according to the invention, indicated overall as 1, comprising a central unit 20 connected to at least one device 30 for detecting the posture adopted by the sow 40. This posture can be a standing posture 41 or a lying posture 42.

The detector device 30 comprises at least one proximity sensor 31. In this way, the sensor 31 is always turned toward the dorsal side of the sow and, therefore, it can determine the sow's standing 41 or lying 42 posture. Obviously, the detector device can be mounted alternatively on the side of the cage, so that the proximity sensor is pointed at the flank side of the sow, rather than its dorsal side.

The proximity sensor 31 is preferably installed in a transparent plastic cover of a monitoring device 32 mounted on the bar of the detector device 30. The sensor 31 has a memory as well as a detection and control card for communication with the central unit 20.

The detection and control card (not shown in the figures) comprises a processor (not shown in the figures) which acts as a means of acquisition of the activity of the sow, for example, the processor connected to the sensor and a permanent memory, appropriately programmed, able to record the total time within a predetermined time period during which the sow 40 is standing and to provide the time of standing to the central unit 20.

The central unit 20 contains a communication interface 21, which is connected to a plurality of monitoring devices 32 and processor 22, for the data detected at the various detector devices 30 mounted on the respective cages. The central unit 20 further comprises a power pack (not shown in the figures) to power the electronic components of the various detector devices 30 connected to the central unit 20.

Finally, the central unit 20 has a user interface device 23, by which the data acquired and/or processed can be displayed locally to a user. The user interface device 23 contains a software application suitable to displaying the data acquired and/or processed and an I/O interface, for example, of serial type, to allow connection to an input means 61 and to a display 62.

Alternatively, or in addition, the user interface device 23 can contain a network card for remote communication of the data acquired and/or processed by the processor 22. In this case, the display application is installed in the memory of a remote computer, accessible to the user (not shown in the figures), which contains an appropriate communications protocol for exchanging data with the network card of the user interface device 23.

The processor 22 comprises a memory in which appropriate software is installed, easily implemented by the practitioner in this field, containing instructions to carry out the procedure of the invention, as explained hereafter.

Figure 2:
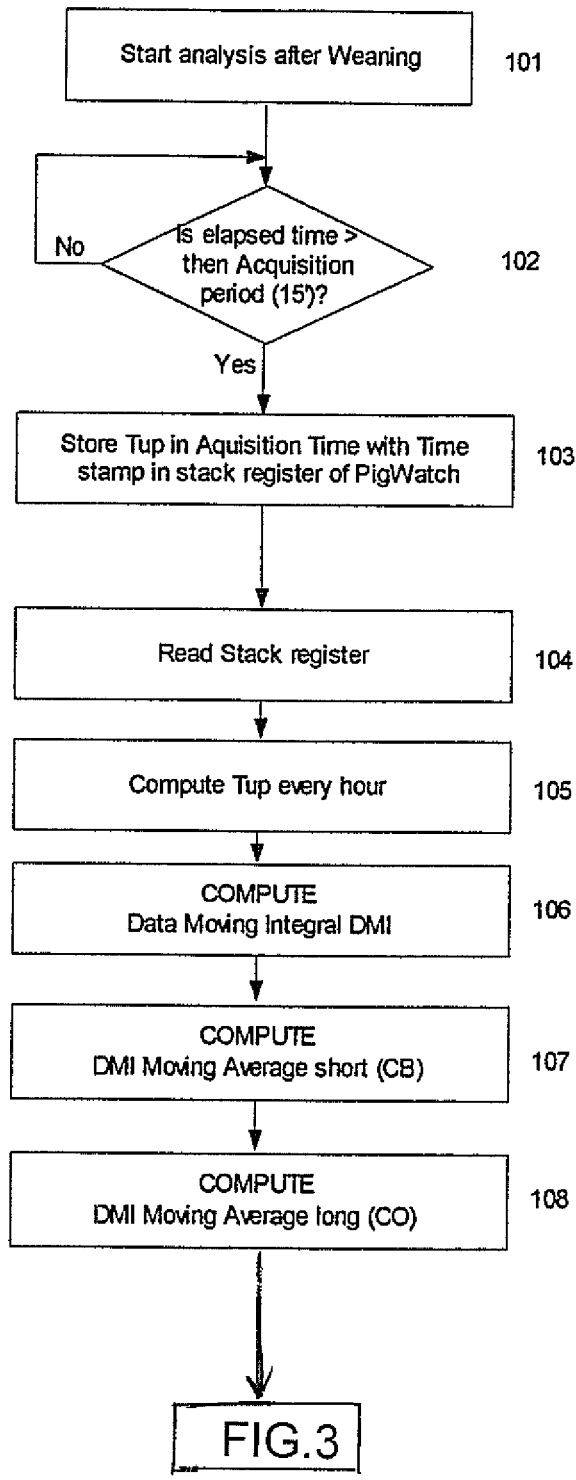
FIGS. 2 to 10 show elements of the algorithm used in the apparatus of FIG. 1.

In an initial step 101 of FIG. 2, after each sow has been placed in its own cage 50, an identification number SIN ("Sow Identification Number") is assigned to each detector device 30, that is, to each sow, and all the data pertaining to the sow will be labelled by this. The sows are generally placed in the cages right after weaning.

In step 102, the control card of each detector device 30 collects the time $T_{UP}$ in which the sow was standing in the past period of sampling (for example ten minutes). This datum, measured in seconds, is stored in a stack (step 103) of the control card with the time stamp of the end of the fixed period of sampling (for example at the end of every 10 units: in any case the period of sampling is an integral sub multiple of an hour).

In step 104 and 105, the data is acquired from the start by the central unit 20, and accumulated in a period of one hour. The reason of the granularity in the device 30, that uses as period of sampling a sub multiple of one hour, is due to the fact that by using more granularity, the control card 30 is able to detect if the IR sensors are dirty.

In step 106, the processor 22 integrates the data acquired on the basis of a first interval of time, preferably equal to 24 hours, and discards from the integration the older data, that is, the six detections (in case of a sampling period of 10 minutes) occurring in the 24$^{th}$ hour prior to the hour of integration. The integration and the discarding of the older time data is preferably done and stored in memory every hour, so that the respective integral is associated with each hour, in memory.

The calculation done in step 106 constitutes a moving integration and it is effective at performing a first filtering of phenomena extraneous to heat that influence the time when the sow is standing, for example, the periods of feeding, when all the sows are in the standing posture, or periods when a stranger enters the sow barn, and so forth.

With the moving integration, at every hour from the placement of the sow in the cage one integrates the data of the preceding 24 hours and uses these data to obtain a pre-distribution of the state of agitation of each sow. It has been found that, after 24 hours from the placement in the cage, the data moving integral (DIM) is weighed and only the continuous variations, such as those involving the stress of heat, can create significant changes in the course of the moving integral DIM.

The phenomena of short duration, such as feeding, watering, or entry of personnel unfamiliar to the sows, are in this way filtered out, avoiding automatic misinterpretations of the stress phenomenon on the part of the apparatus of the invention.

To improve the interpretation of the data acquired, the central unit 20, again through the processor 22, performs each hour a calculation of two moving averages of the data moving integral DIM (steps 107 and 108): a moving average of short step (CB) and a moving average of long step (CO). Preferably, the short moving average CB is calculated over the past 7 hours, while the long moving average CO is calculated over the past 12 hours. In this way, the two values CB and CO calculated and stored in memory can be used to determine a trend, positive or negative, of the state of stress of the sow, independently of the stress thresholds normally chosen in arbitrary fashion in the prior art.

The moving averages CB and CO are calculated every hour and, through the user interface device 23 of the central unit 20, CB and CO are displayed on the user display 62 on the same graph.

Figure 3:
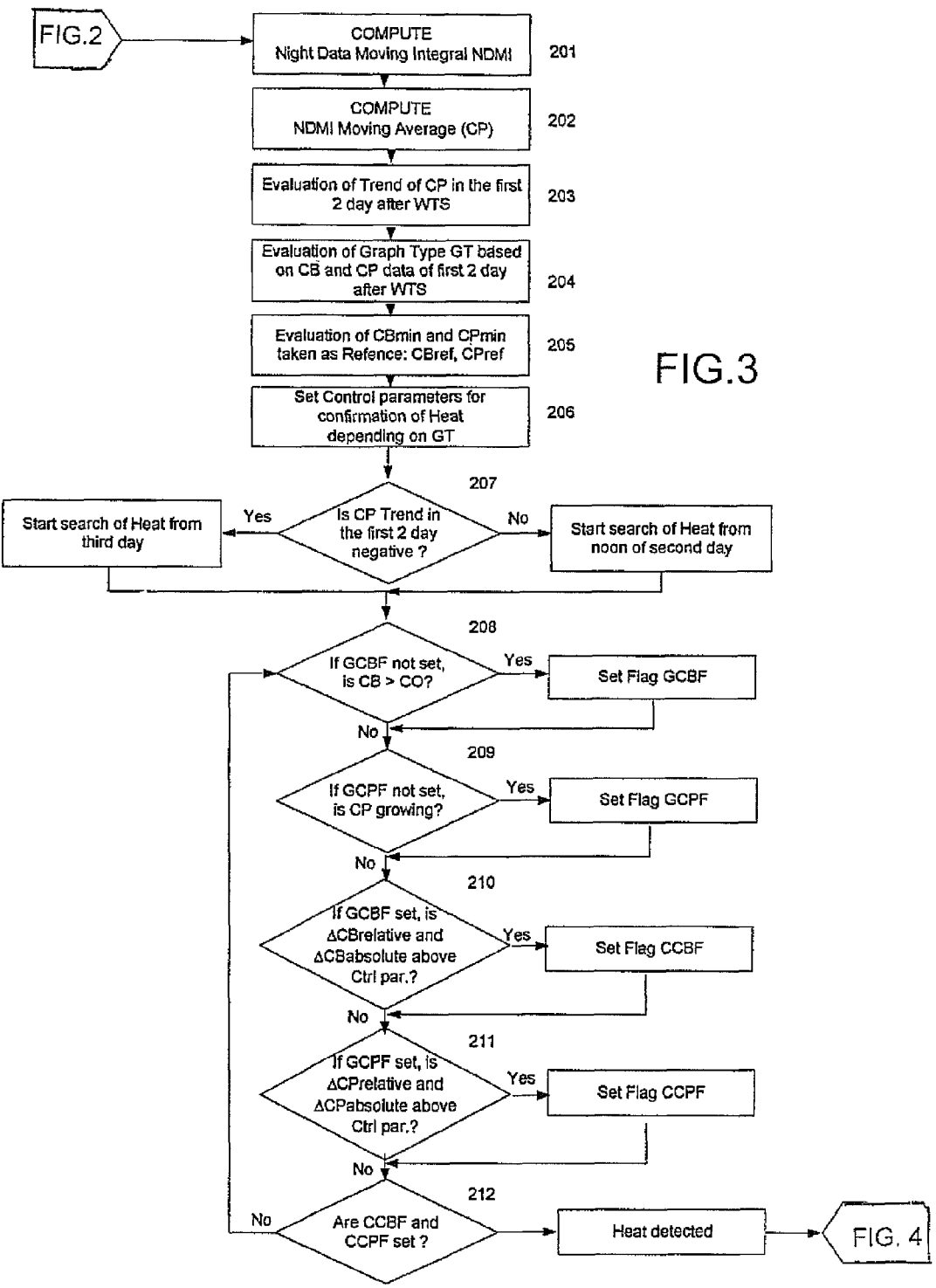
Figure 4:
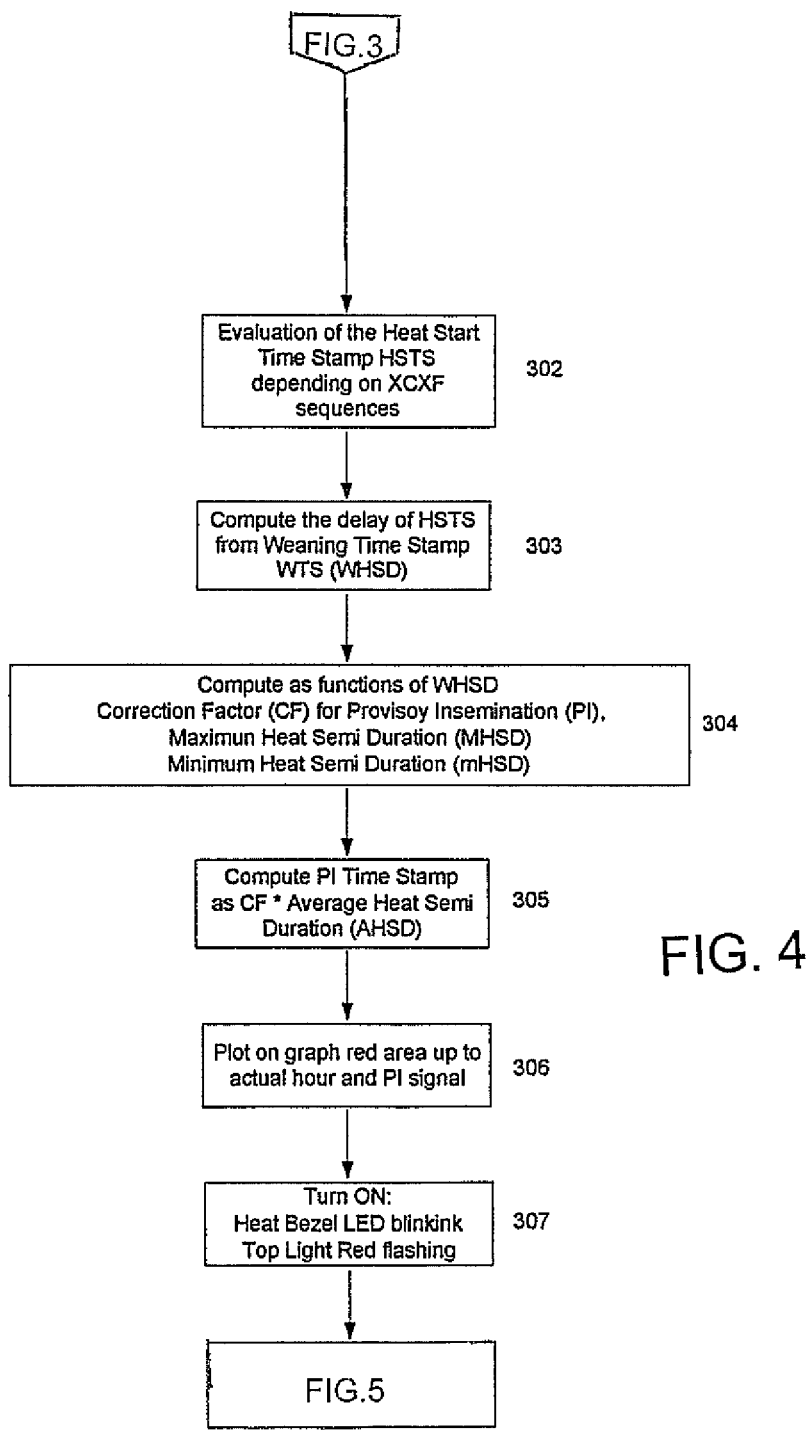
Figure 5:
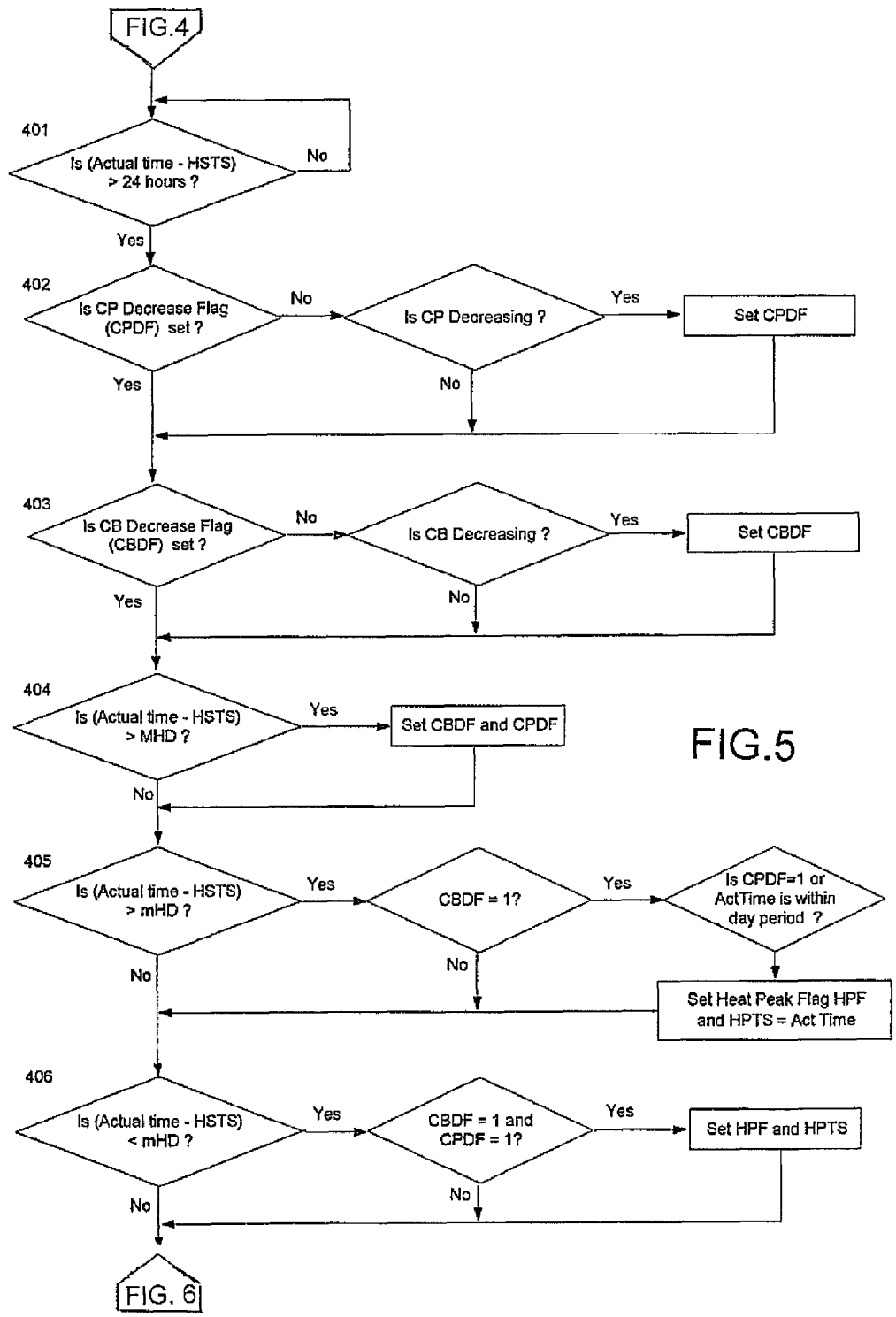
Figure 6:
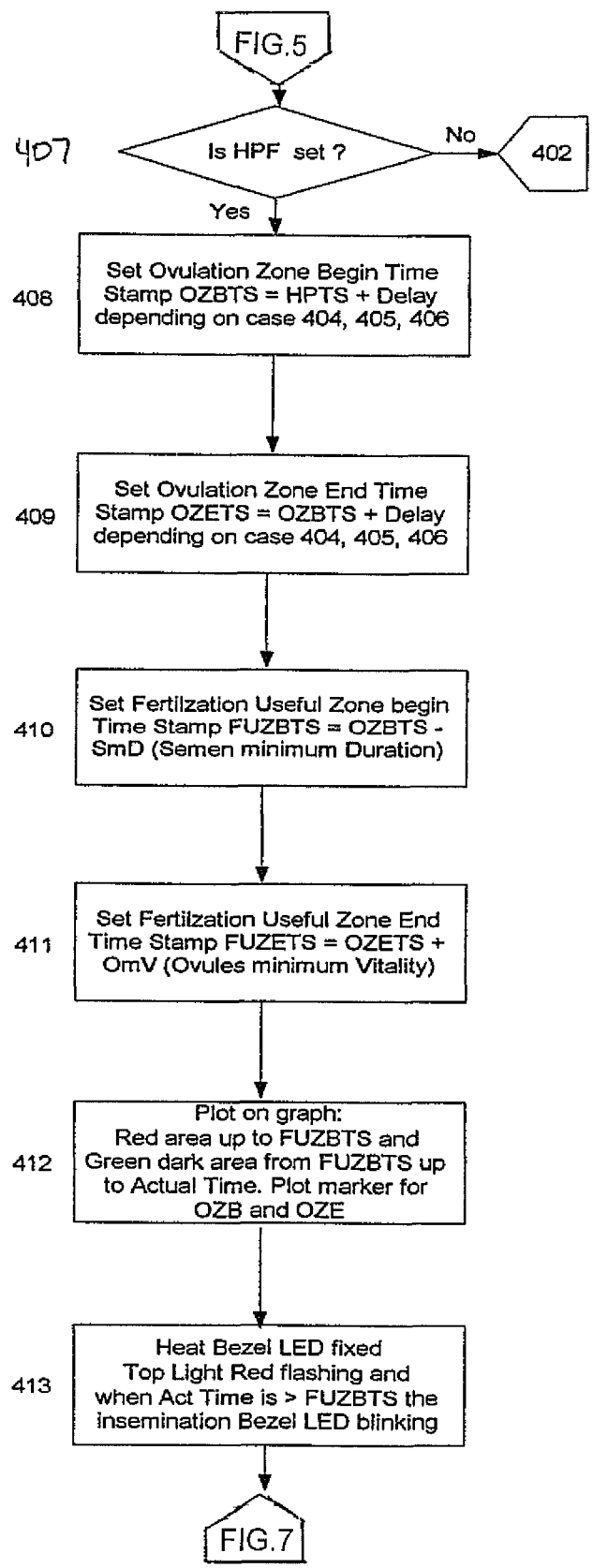
Figure 7:
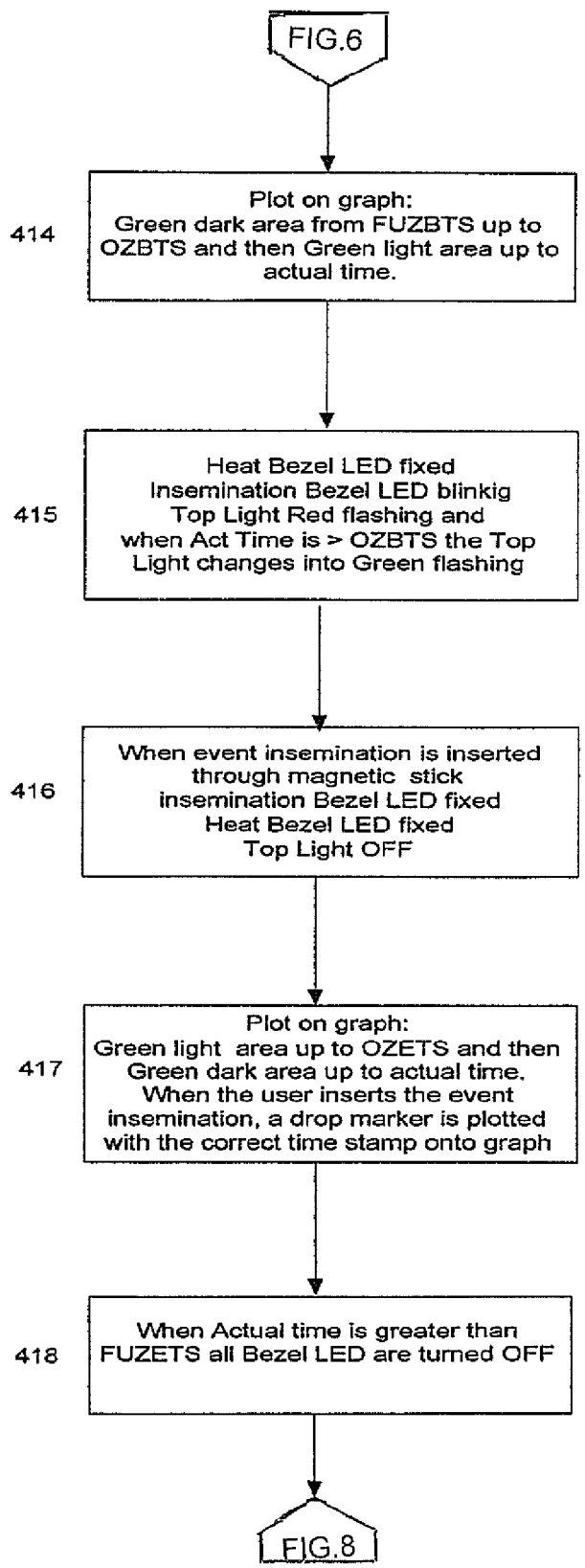
Figure 8:
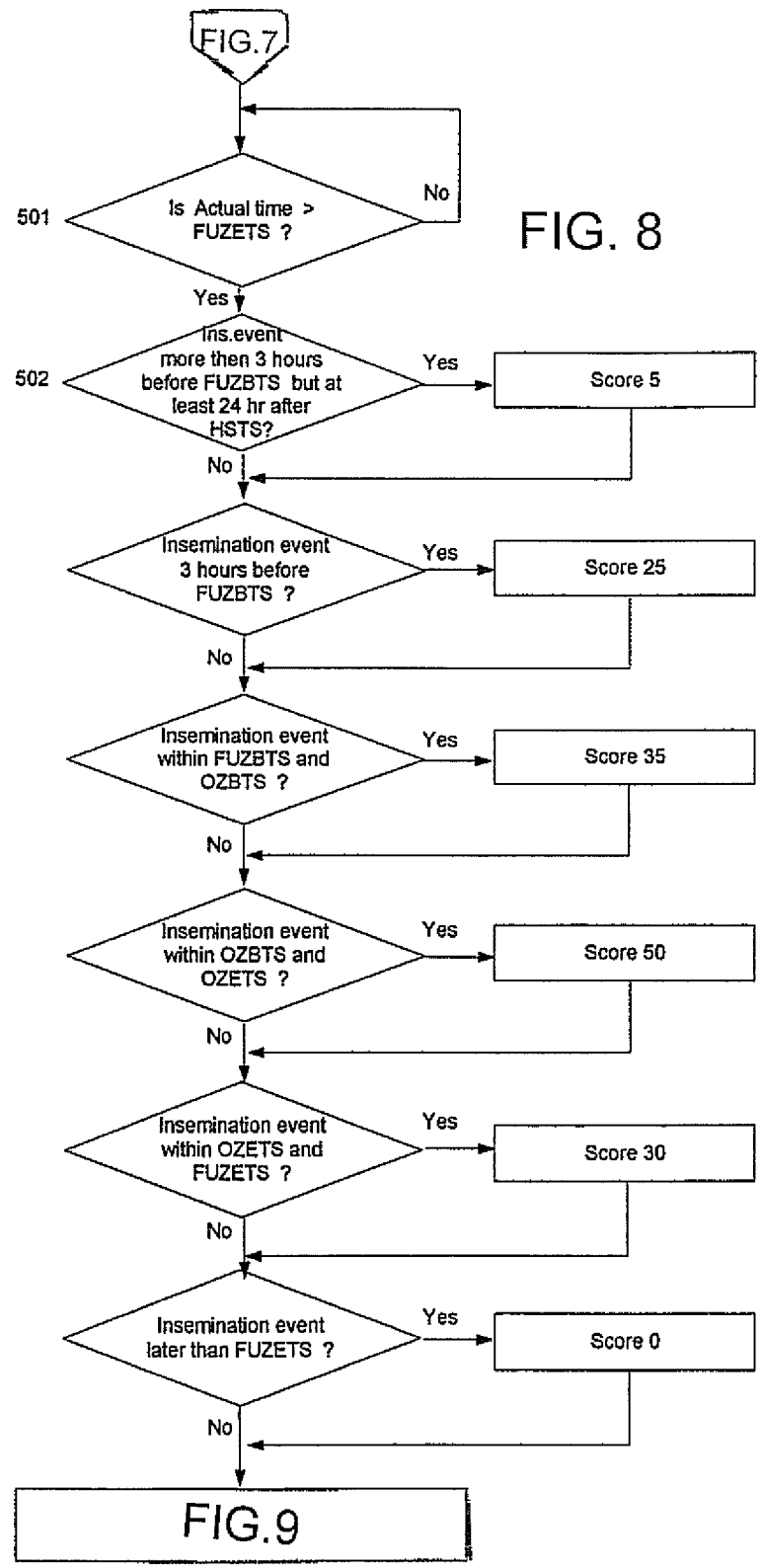
Figure 9:
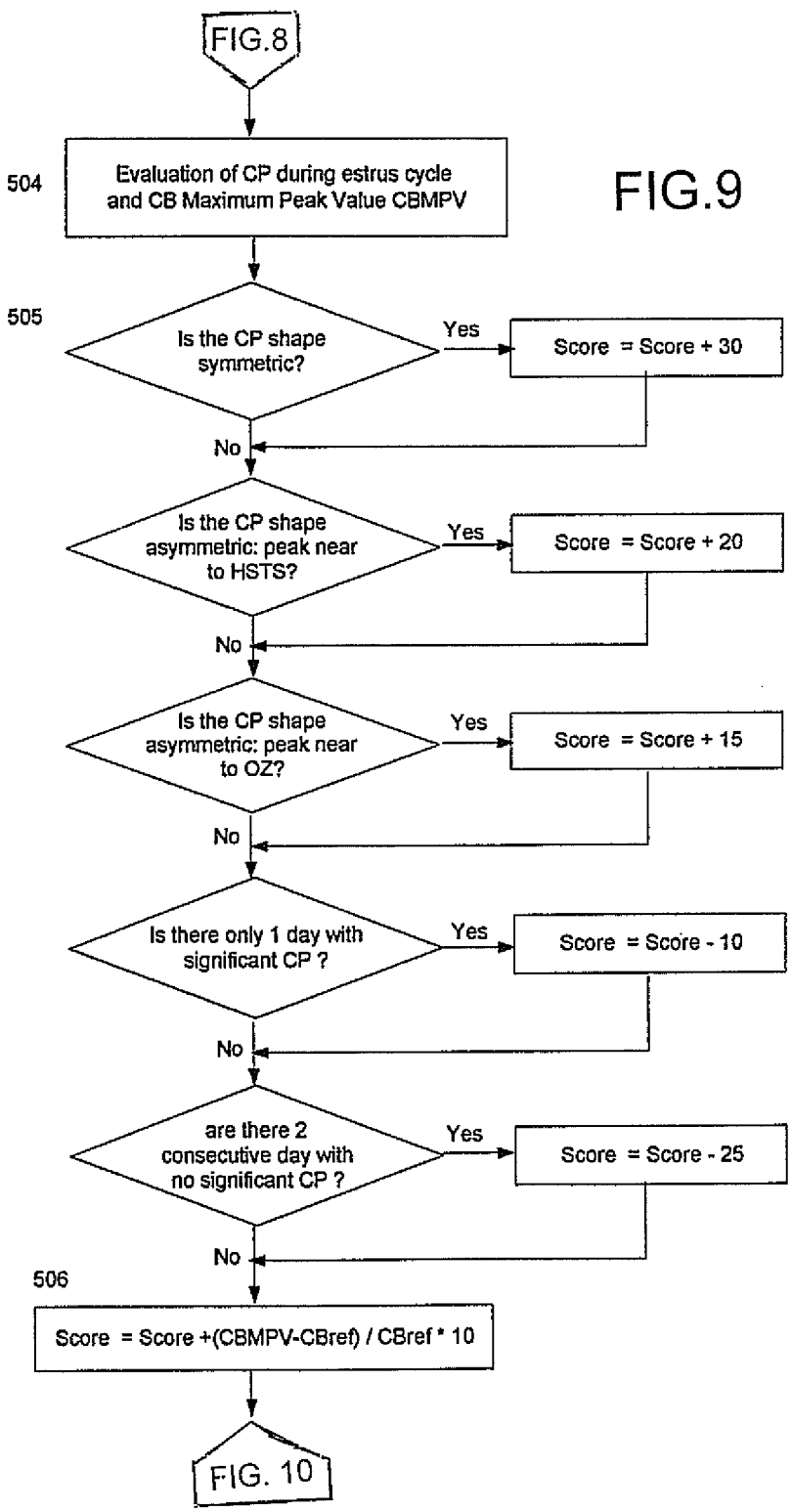
Figure 10:
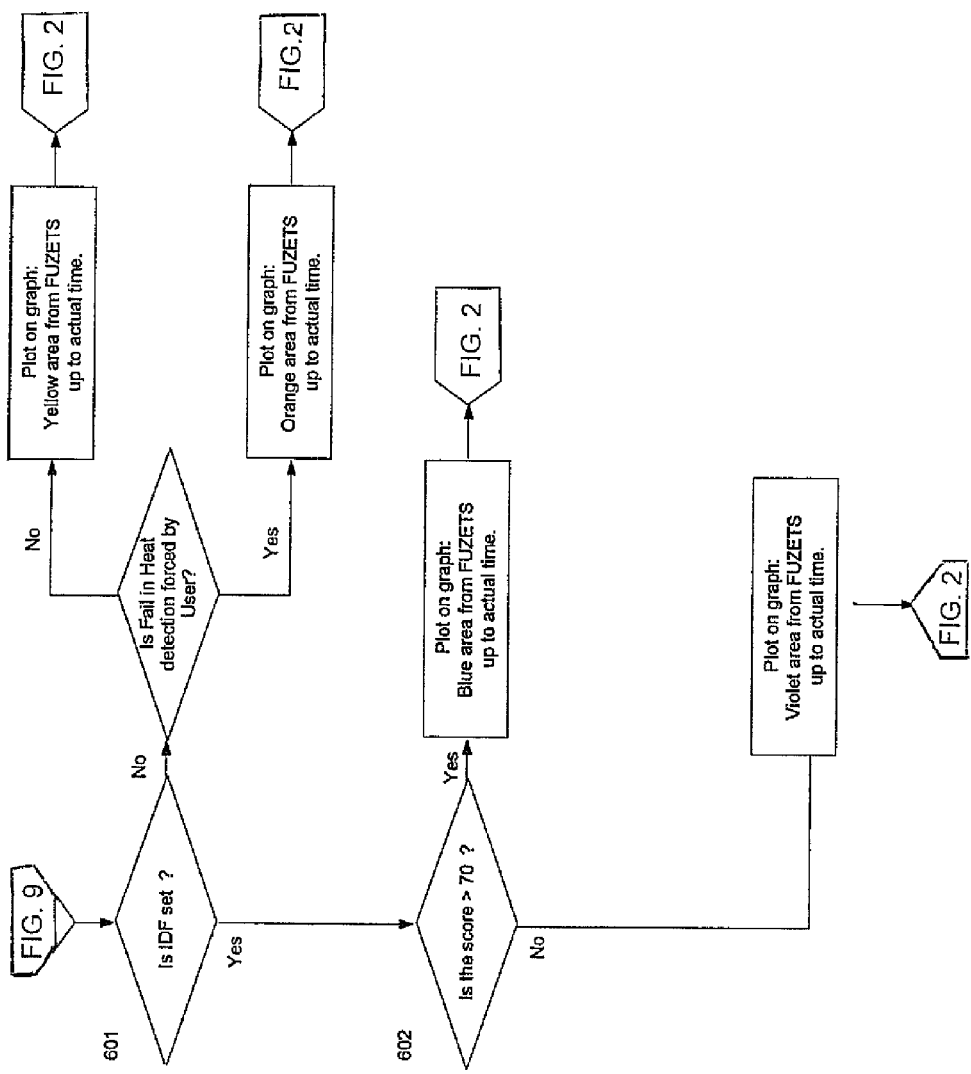

In FIG. 3 step 201 the processor 22 integrates the data acquired during the night period on the basis of a first interval of time, preferably equal to 24 hours, and discards from the integration the older data, that is, the six detections (in case of a sampling period of 10 minutes) occurring in the 24$^{th}$ hour prior to the hour of integration. The integration and the discarding of the older time data is preferably done and stored in memory every hour, so that the respective integral is associated with each hour, in memory, the resultant integration is called NDMI (Night Data Moving Integral).

In step 202, to improve the interpretation of the data acquired, the central unit 20, again through the processor 22, performs each hour a calculation of a moving averages of the night data moving integral NDMI (called CP). Preferably, the moving average CP is calculated over the past 12 hours.

In step 203, the central unit 20, again through the processor 22, performs an evaluation of the CP trend in the first 2 days after WTS.

In step 204, the central unit 20, again through the processor 22, performs a classification of the graph according to:
the intensity of the activity in daily and night period, shown by CB in the first two days after WTS,
the intensity of the activity only in night period, shown by CP in the first two days after WTS,
the trend of CP in the first two days after WIS.

The classification is called Graphic Type (GT), there are 27 different GITs, and according to this are set control parameters that ΔCB relative, ΔCB absolute, ΔCP relative, ΔCP absolute must satisfy to get the Heat determination confirmation (step 206).

In step 205, the central unit 20, again through the processor 22, computes the minimum value of CB (typically in the second day after WTS) called CBmin and the CPmin (typically in the second day after WTS, but may be in the first day depending on trend type of the graph). These values are taken as references (CBref and CPref) for evaluation of ΔCB relative, ΔCB absolute, ΔCP relative, ΔCP absolute in the following steps 210 and 211.

In step 207, the central unit 20, again through the processor 22, evaluates when the heat determination starts according to the trend of CP shown in the first two days. If the trend is negative, the search of heat will start from the 0:00 of the third day, because there is a clear discontinuity, between the first stress (due to the moving of the sow from weaning to the new stall) and there is no need to start before, otherwise in case of trend type positive or flat (typically 20% of the cases) the start of the search of weaning will start from noon of the second day.

In step 208 or 209, the central unit 20, again through the processor 22, evaluates if there is an increase of CB and CP if and when this increase is it found it will set the relative flags GCBF (Growing CB Flag) and GCPF (Growing CP Flag). The increase in CB is detected comparing the ordinate of CB to the ordinate of CO, to set the flag CB must be greater than CO for at least three hours. The increase in CP is detected when the actual CP is increasing more than a fixed percentage with respect to the previous value, measured three hours before. When a Flag is set the algorithm stops to search for a first increase and looks for a confirmation procedure steps 210 and 211.

In step 210 and 211, the central unit 20, again through the processor 22, computes every hour the value ΔCB relative, ΔCB absolute, ΔCP relative, ΔCP absolute and compares them with the control parameters defined in step 206. When both control parameters are met for CB, it sets the Control CB Flag (CCBF); when both control parameters are met for CP, it sets the Control CP Flag (CCPF).

In step 212, the central unit 20, again through the processor 22, when both CCBF and CCPF are set, is able to confirm a heat and start to look for the best time stamp for the heat start HSTS. For this, it evaluates the sequence of flag GCBF, GCPF, CCBF and CCPF and according to the resultant sequence and the time distance between these flags, it is able to define the best HSTS in step 302. In step 303 it evaluates the delay between WTS and HSTS, this delay is called WHSD (Weaning to HS Delay). WHSD is used in step 304, to evaluate the Maximum Heat Semi Duration (MHSD), the minimum Heat Semi Duration (mHSD) and a Correction Factor (CF). This CF is used in step 305 to evaluate the best Provisory Fertilization Time Stamp (PITS) that is evaluated using the Average Heat Semi Duration (AHSD), computed by central unit 20, again through the processor 22, on all Heat Semi Duration registered from the previous sow cycles. The AHSD is an important data, because it depends on the management system of weaning used by a farmer, so it can change depending on the farmer. This is the reason why the algorithm prefers to compute it instead of using a standard value. The evaluation of PITS is done with this formula PITS=CF*AHSD. When PITS is ready, central unit 20, again through the processor 22, in step 306 plots on a graph a red area (that means Heat) starting from HSTS up to actual hour, and PI signal (a green arrow with hour stamp) located below the time axis at the correct time stamp. This information will be very useful to the farmer, because in advance (many hours before the ovulation will be) it can say roughly when the best timing for fertilization will be. Because the ovulation is uniformly distributed in the 24 hours of the day, the farmer will know in advance if the best timing zone for fertilization will be during the shift or outside it, in this case he can carry-out an earlier fertilization before the end of the working shift. This fertilization, due to the semen duration, may be good enough to get the sow pregnant. This matter will be better discussed in below points.

In step 307, the central unit 20, again through the processor 22, sending command to the control card of detector device 30, will turn ON in blinking mode the red bezel LED and the Top Light red in flashing mode, indicating heat start. In this way, also the workers are informed about the state of heat of a sow.

Starting from step 401, the central unit 20, again through the processor 22, starts after 24 hours from FISTS to determine the Heat Peak. In step 402, when it detects a CP decreasing, sets the CP Decreasing Flag (CPDF). In step 403, when it detects a CB decreasing, sets the CB Decreasing Flag (CPDF). When a Flag has been set, the algorithm stops to search for other decreases of the related curve. The algorithm runs continuously from step 402 to 407 until the condition of Heat Peak has been determined. The condition may be reached if:

Step 404, if the actual time has a delay from HSTS more than MHD, CBDF and CPDF will be forced to 1. This allows the algorithm to set the Heat Peak Flag (HPF) in the following step 405 or 406.

Step 405, if the actual time has a delay from HSTS more than mHD, the algorithm may set the HPF if CBDF=1 and if CPDF=1 or the actual time is in daily period (from 9 am till to 4 pm).

Step 406, if the actual time has a delay from HSTS is less than mHD but more than 24 hours, the algorithm may set the HPF if CBDF=1 and CPDF=1.

When HPF is set, the algorithm is able to plan the time stamp for Useful Fertilization Zone in the Ovulation Zone as described below.

In step 408, the central unit 20, again through the processor 22, plans the Ovulation Zone Begin Time Stamp (OZBTS) adding to HSTS a delay 1 that depends in what condition (404, 405 or 406) the HPF has been set to.

In step 409, the central unit 20, again through the processor 22, plans the Ovulation Zone End Time Stamp adding to OZBTS a delay 2 that depends on what condition (404, 405 or 406) the HPF has been set to.

In step 410, the central unit 20, again through the processor 22, plans the Fertilization Useful Zone Begin Time Stamp (FUZBTS) tracking from OZBTS the Semen minimum Duration (SmD) expressed in hours.

In step 411, the central unit 20, again through the processor 22, plans the Fertilization Useful Zone End Time Stamp (FUZETS) adding to OZETS the Ovules minimum Vitality (OmV) expressed in hours.

In step 412, the central unit 20, again through the processor 22, plots on a graph a red area that means heat starting from HSTS up to FUZBTS, and a green dark area from FUZBTS up to an actual time zone of fertilization, and OZB, OZE markers (two green opposite horizontal arrows with hour stamp) located in the mid-ordinate of graph.

In step 413, the central unit 20, again through the processor 22, sending command to the control card of detector device 30, will turn ON in fixed mode the red bezel LED and the red Top Light in flashing mode, indicating heat time zone. When the actual time of fertilization is greater than FUZBTS, the green bezel LED will be turned ON in blinking mode, indicating useful fertilization time zone. In this way, also the workers are informed about the state of Heat Peak of a sow and that they can proceed with fertilization of the sow if wanted.

In step 414, the central unit 20, again through the processor 22, when the actual time of fertilization is greater than OZBTS, plots on graph a red area that means Heat, starting from FISTS up to FUZBTS, a dark green area from FUZBTS up to OZBTS and a light green area from OZBTS up to actual hour of fertilization.

In step 415, the central unit 20, again through the processor 22, when the actual time of fertilization is greater than OZBTS, sending command to the control card of detector device 30, will turn ON in fixed mode the red Heat bezel LED, the Top Light will be changed in green flashing mode. The green fertilization bezel LED will continue to blink. In this way, the worker is informed about the current status of Ovulation of a sow and knows that fertilization of the sow has to be carried-out as soon as possible.

In step 416, when the worker uses the magnetic stick to enter the event of fertilization, the control card of detector device 30, uses this signal to turn OFF the Top Light and change into fixed mode the green fertilization bezel LED. In this way the worker as a confirmation that the event has been properly processed. The control card of the detector device 30 sends the information of the event "fertilization Done" to the central unit 20, that again through the processor 22, is able to plot a marker onto graph, located in the middle ordinate of the graph, at the correct position of the time axis that looks like a small drop indicating the event "fertilization Done" (step 417).

In step 417, when the actual time of fertilization is greater than OZETS, the central unit 20, again through the processor 22, plots on the graph a red area that means Heat, starting from HSTS up to FUZBTS, a dark green area from FUZBTS up to OZBTS, a light green area from OZBTS up to OZETS and a dark green area from OZETS up to actual hour of fertilization.

In step 418, when the actual time of fertilization is greater than FUZETS, the central unit 20, again through the processor 22, sending command to the control card of the detector device 30, will turn OFF every bezel LED.

In step 501, when the actual time of fertilization is greater than FUZETS, The algorithm starts to analyze the previous situations in order to be able to evaluate a confidence level on what has happened.

In step 502, the central unit 20, again through the processor 22:
If the fertilization Event has occurred more than 3 hours before FUZBTS but at least 24 hr after HSTS, it sets a score to value 5 and sets the fertilization Done Flag (IDF).
If the fertilization Event has occurred less than 3 hours before FUZBTS, it sets the score to value 25 and sets the fertilization Done Flag (IDF).
If the Fertilization Event has occurred within FUZBTS and OZBTS, it sets the score to value 35 and sets the fertilization Done Flag (IDF).
If the fertilization Event has occurred within OZBTS and OZETS, it sets the Score to value 50 and sets the Fertilization Done Flag (IDF).
If the Fertilization Event has occurred within OZETS and FUZETS, it sets the score to value 30, the score is not changed if already set to the higher value, and it sets the Fertilization Done Flag (IDF).
If the Fertilization Event has occurred later than FUZETS, it sets the score to value 0, the score is not changed if already set to highest value, and it sets the Fertilization Done Flag (IDF).

In step 504, the central unit 20, again through the processor 22, evaluates the trend of CP shape within the HSTS and FUZETS and CB maximum Peak value (CBMPV) within the same period.

In step 505, the central unit 20, again through the processor 22 sets:
The score=score+30 if the CP shape Trend is symmetric.
The score=score+20 if the CP shape Trend is asymmetric with the peak near to HSTS.
The score=score+15 if the CP shape Trend is asymmetric with the peak near to OZBTS.
The score=score−10 if there is for one day only a significant CP.
The score=score−25 if there are two days without a significant CP.

In step 506, the central unit 20, again through the processor 22, evaluates the factor (CBMPV−Cbref)/CBref*10 and adds the result to the score value: the score=score+((CBMPV−Cbref)/CBref*10). This factor may range from 8 to 20 and the greater it is, the more it means that the heat has been consistent.

In step 601, the central unit 20, again through the processor 22, checks if the IDF (Fertilization Done Flag) has been set. If not set it checks if the user has entered an event of Fertilization Negated because there is a Failure in Heat Detection (HFDF: Heat Failure Detection Flag) and then:
If set a HFDF, there is plotted on graph an orange area starting from FUZETS up to the actual time.
If not set a HFDF, there is plotted on graph a yellow area starting from FUZETS up to the actual time.

In step 602, the central unit 20, again through the processor 22, if the IDF (Fertilization Done Flag) has been set and:
If the score is greater than 70, there is plotted on graph a blue area starting from FUZETS up to the actual time, with the value of the score in white colour, located in the middle ordinate of graph.
If the score is lower than 70 there is plotted on graph a violet area starting from FUZETS up to the actual time, with the value of the score in white colour, located in the middle ordinate of graph.

It has been proven in practice that the arrangement disclosed herein implements a practical procedure able to provide an effective determination of the onset of the state of heat of a sow and an estimate of the time of fertilization much earlier than that of the currently known methods and, what is more, it is effective in also determining the state of heat of any sows or gilts at any time and in any location in any sow barn.

Besides this, the proposed method is also effective in the analysis of data pertaining to the state of agitation of the sow, sampled at any time of the day or night.

The invention so designed is capable of many modifications and variants, all of which come under the concept of the invention; moreover, all the details can be replaced by other technically equivalent elements.

There is a trend in management of sows that the sows are not to be confined in stalls after they are released from the farrowing crate, and thus are housed in free penning which allows them to move around. Thus a fixed sensing system which uses a proximity sensing device is only usable where the animal is individually confined in stalls. In free penning an alternative arrangement for detecting standing is used and many different arrangements are suitable for this function.

Thus in one example a device can be placed on the bottom of the sow body with a band to fix it just after the front leg which uses a distance detector to check the distance from the floor.

An alternative device can be fixed on a leg and may be an inclinometer which measures when the animal changes in orientation from standing to lying. Pressure switches can be used to detect when the animal is lying.

Other devices can be used for detecting characteristics of the animal which are indicative of estrus, for example the beat of the heart.

The device itself may contain the microprocessor with the built-in algorithm, the microprocessor communicating to a PC in wireless mode. In this case the device may communicate only the events, like Start of heat, start of Useful fertilization Time Zone, start of Ovulation, start of Preferred Fertilization Time Zone, end results of confidence level. The device may not provide direct visual information to the breeder to save energy, but only on a PC. Alternatively the device may have all the functions described herein. Yet further, the device may communicate only the data of the time of standing and lying with all processing being done at the central location.

The method described above is primarily designed for sows returning from farrowing but it will be appreciated that the same system may be applied to gilts and even to sows that experience heat returns due to illness or miscarriage during their first phase of gestation. Also where fertilization fails at the first estrus, the animal may be monitored through the second estrus.

The device can be used to determine any first or second estrus. Other arrangements are not able to do this, because their determination of estrus is obtained only by a comparison of the proportion of standing time during the night against a fixed threshold. Furthermore after the weaning there is a period of stress when a sow is moved around, which has to be excluded from the detection process by a suitable filtering part of the algorithm.

The present arrangement uses a strategy where firstly all the raw data is processed to obtain a continuously graph of the 24 hours of standing time and night time standing. Second it uses data of the first 2 days after the weaning to characterize what kind of sow is present, that is a sow that usually stands up more or less, a sow that has poor activity during the night or good activity. From this analysis the algorithm acts to classify the sow into a number of different predetermined types obtained by prior analysis and contained in a memory and uses strategy tailored for every different type. This system is very powerful because it is able, through this classification, to normalize data and remove the need of fixed threshold in determining the six main goals, which are Estrus status, Estrus Start Time Stamp (FISTS), Estrus Peak, useful fertilization time zone where one can start fertilization the sow with success, the zone where, with the highest probability, the ovulation will take place, and the actual time where the preferred fertilization will be suggested.

Furthermore when the cycle of estrus is completed, the system is able to give a confidence level about the correctness of the predictions and it will indicate possibly by colors on the graph if the fertilization has been done within the optimum time period as determined by a 24 hour graph and night graph after the peak of estrus or by different colors when the confidence level is poor so that the confidence is below 60%.

The system predicts the best time for fertilization within the period of ovulation.

The system takes into account working periods to determine the best time for fertilization. This is done by, just after the estrus determination, which means within the first 30 hours max of the estrus, planning a provisory fertilization time zone, that roughly can tell if the ovulation time zone will be out of the working shift period or not. If the provisory fertilization time is planned for the night period, when the work shift is over, and the useful fertilization zone is already active, the farmer may plan an early fertilization before leaving the farm, in this way he is able to ensure that the sow has been fertilized in due time. The next morning he is able to determine from the graph information if there is a need for a second fertilization or not.

The system is able to determine:

The ovulation time zone, within 30 hours from the beginning of estrus phenomena.

A useful fertilization time just after the estrus detection.

The estrus start time stamp just from the $2^{nd}$ day after the weaning.

The estrus peak.

The ovulation time zone.

The optimum fertilization time within the ovulation zone.

The correctness of the pattern when the estrus is completed.

The sensor unit 30 includes a light display system 32A arranged to provide an indication by illuminating a suitable Light or LED or of Light or LED patterns indicative of: useful fertilization time zone, preferred fertilization time within the time of ovulation, completion and registration of fertilization, alternative early or late fertilization time for out of working shift applications, and illness or weakness of the animals.

The indicating system can be arranged to provide the following information

Heat Start: Blinking Red

Heat Peak: Steady Red

Provisory Insemination Vs Last Hour of Working Shift; Blinking Red and Green

Beginning of Useful Fertilization Zone: Blinking Red and Green

Beginning of Ovulation Zone: Slow Blinking Green

Peak of Ovulation Zone: Fast Blinking Green

End of Useful Fertilization Zone: Fast Blinking Green

Provisory Fertilization Vs First Hour of the Morning: Fast Blinking Green

Sow that has been Fertilized and Entered into the System Vs Magnetic Stick: Steady Green This can be achieved by the following:

Heat start: PI Vs Last Hour of Working Shift: 1 flash red and 1 flash green every 2 second if an insemination done steady green (see task 121)

Heat peak: 1 flash red every 2 second if an insemination properly done steady green From FUZBTS: 1 flash red and 1 flash green every 2 second if an insemination properly done steady green From OZBTS: 1 flash green every 3 second if an insemination properly done steady green From OZPTS till to task 710: 1 flash green every 2 second if an insemination properly done steady green Sensor dirty: Sensor Yellow LED of Bezel slow blink 1 times per second Disease state: Sensor Yellow LED of Bezel fast blink 3 times per second.

The unit 30 also includes an input system 32B such as a magnetic stick operable by the worker to provide an input to the system indicative of an actual time of fertilization.

In the event that the fertilization is later found to have failed, the system provides an indication about whether the actual time of fertilization occurred at the indicated preferred time of fertilization within the time zone of ovulation.

The indicating system 32A is arranged to provide a first signal when a change is detected indicative of estrus and of a useful fertilization time zone, a second signal indicative of peak of estrus, a third signal indicative of commencement of the time of ovulation and of a preferred fertilization time, a fourth signal indicative of alternative early or late fertilization time for out of work shift applications, a fifth signal indicative of completion and registration of fertilization, and a sixth signal indicative of illness or weakness of the animals.

The indicating system 32A includes a countdown digital clock 32C which is arranged to provide to the worker a countdown indication of time of the preferred time zone of fertilization.

The system is able to detect if an IR sensor is dirty, this information is shown on a led on a bezel of the device and also on the icon of the stall in the monitor panel of the user interface. When the sensor is cleaned by the user, the system will restore automatically the warning signals both on the device and monitoring panel.

The event of fertilization, which has been carried out by the user, is entered through suitable input device such as a magnetic stick which is very simple to use. The system will enter automatically this event with the correct time stamp. It will be appreciated that some operators will prefer to carry out fertilization at a time determined by themselves based on other characteristics and their own experience. This time may differ from the time predicted by the system. This actual time of fertilization can be entered and later when the estrus is completed and all data available for analysis, the system can provide an indication of the confidence level based on a comparison of the actual time and the calculated optimum time.

The event of change of sow in a stall, may be entered through a suitable input device such as a magnetic stick which is very simple to use. The system will enter automatically this event with the correct time stamp, closing the previous cycle and opening the new one. Later, the farmer may insert the correct code of a specific sow, if he wants to use the device to generate and store historical data relating to the sows throughout their repeated pregnancies.

The system does not need any adjustment after installation, and the algorithm, through the standing time graph classifications is able to find automatically the estrus and the time for fertilization.

The system can also be used for determining illness or weakness in the animal. First the device can determine during the feeding or drinking if the sow is down, which means that something is wrong with the sow. Thus when feed is supplied to the animal in the stall at a trough 10, the device can be used to determine whether the animal stands to feed or drink. If not, a stimulation can be applied to encourage the animal to stand to feed and eat. Also, if a sow in a farrowing pen becomes too weak to feed or drink adequately, leading to possible malnourishment for the piglets, the sow can be stimulated to feed.

The information can all be displayed on a PC at the location or remote for analysis by persons outside the specific barn where the animals are located. Also a hand held device can be used for display to the worker in the barn to supplement or replace the information displayed at the device on the stall or on the animal. All information can be printed as required for storage, transfer or management purposes.

The arrangement described herein provides a computerized AI management system that allows the user to inseminate sows exactly at the right moment, every time, all the time. Thanks to the system's 24/7 electronic sow behavior analysis capability, the user can monitor in real time the heat status of each sow.

The programming of the three daily insemination sessions should be done in accordance with the gestation barn staff's work shift. The ideal work shift would be something like 6:00 a.m. to 10:00 p.m., but the system still works quite well with a 7:00 a.m. to 5:00 p.m. schedule. Those three insemination sessions should be strategically spread out throughout the day, so that the first one takes place as early as possible when the workers start their morning shift, the second one at the beginning of the afternoon and the third one, at the last hour of the work shift. In a 4-week batch weaning type of management, the sows are typically inseminated over a period of 5 to 6 days, leaving only a few days per month where workers need to be in the barn in the evening to inseminate on day 4, 5 and 6. In such a case, in order to optimize results, it is highly recommended to schedule a work shift that extends to 10:00 p.m.

Post-weaning sow stimulation through boar exposure is known to be very important to help trigger sow's heat cycle, and detect early heat cycles. In this perspective, the worker needs to bring the boar in front of each sow for a good boar-to-sow snout-to-snout contact. For good stimulation, expose the boar to each sow for about 15 to 30 seconds. This operation is to be done once a day during the first three post-weaning days. Using a remote-controlled motorized boar cart allows for quick, easy and efficient post-weaning sow stimulation and requires only one worker.

Graph colors subsequently change to identify the current stage of the sow's heat cycle. It gradually passes from white to yellow, to orange, to red, and then to blue or pink at the end of the cycle. The graph respectively turns blue when the score is higher than le minimum score programmed in the system, but turns pink if lower. The score that is displayed on the graph at the end of a cycle broadly reflects the success level of one or more inseminations, in reference with respective insemination requests prompted by the system. See Picture 1.

Usually on day 2 and occasionally on day 3 and 4, the system prompts the worker to confirm the heat status of some specific sows. When the case arises, <<R>> appears on the stall icon on the computer panel, an <<eye>> icon appears on the graph, and <<R-C>> is shown along with the sow and stall number on the insemination worksheet. Most heat check requests are prompted in the morning and must be responded to at once when performing early morning sow stimulation, but some heat requests may be also prompted at other times of the day, The worker can optimize his time and efficiency by regrouping those additional heat check requests, and carrying them-out at the same time of his next planned insemination session, which means either at the beginning of the afternoon, or in the last hour of his work shift. The worker should then confirm which sows were found in heat, by registering in the system the exact time the heat check was performed for each specific sow. Responding to <<R>> requests allows the worker to identify those odd sows that cycle very early after weaning, and to inseminate them as per requested by the system. The number of prompted <<R>> requests depends upon several factors and may vary from herd to herd, and even from one weaning to another one in the same herd.

There are 2 types of insemination requests, respectively called standard and preventive requests, which are prompted in 3 different ways by the system to facilitate the task of gestation barn workers:

1. The stall monitoring device top light blinks green (standard), or red (preventive), respective of insemination request types.
2. The printable insemination worksheet lists all insemination requests, sow and stall numbers.
3. The computer panel stall icons display green or red color floating strips, and every individual sow graph shows an insemination request time flag, respective of insemination request types.

In a Standard insemination Request, the stall monitoring device top light blinks green. The system is programmable for three daily insemination sessions. To ensure the success of an insemination, the worker must carry it out within 4 hours after an insemination request has been prompted. If an insemination request is prompted outside the time frame of those three planned insemination sessions, and if there is no insemination session scheduled within the next four hours, a narrow dark green strip is displayed at one end of the stall icon, indicative of the urgency to do this insemination without any delay.

In an end-of-shift preventive insemination request, the stall monitoring device top light blinks red. Such insemination preventive requests are always prompted one hour before the end of the work shift that is scheduled in the system. The objective is to anticipate insemination requests that are likely to be prompted by the system during the period where there is no worker in the barn, and to carry out respective insemination as a preventive measure before leaving the barn. In some cases, it might be necessary to do a second insemination the next morning to optimize results, but only if requested by the system. The worker should carry it out within 4 hours after an insemination request has been prompted.

In regard to heat check request <<R>> subsequent to first insemination, to optimize results following a first insemination, the system may in some cases request a second insemination and prompt the worker to check if a sow is still in heat before doing it. In such a case, <<R>> is displayed on the stall icon of the sow and the type of request is identified as <<R-R>> on the worksheet. If the sow is still showing clear signs of heat, the worker should inseminate it promptly and the system interprets the registration of the insemination in the system as a confirmation of the heat status of the sow.

The system has been specifically designed to determine the best moment of insemination of newly weaned sows, which represents about 70% of the total inseminations of the herd. The time that is saved using the system allows workers to spend more time and bring more focus on the traditional heat detection of gilts, heat returns and empty sows.

There is also provided a button for indicating by the worker to the system to stop acquiring data (SAD). The operation is based upon the analysis of the natural behavior of sows, which may at times be affected by some occasional workers' activities carried-out in their proximity. Therefore, the data acquisition must be temporarily interrupted, for example, when moving sows in and out, carrying-out some disrupting maintenance work or when performing any other unusual activities that are likely to seriously affect the natural behavior of the sows, The SAD button allows the worker to stop acquisition of data for a period of 1 hour. This SAD button cannot be used more than twice a day and no more than 4 times during the whole cycle of the sow. It is highly advised not to make use of the SAD function after day 4. The system sets a priority for operation which should also take into accounts some odd cases. Thus the insemination requests always take priority over graph colors, no matter what color is appearing on the graph. If an insemination request is prompted, it should be done except if the sow shows no obvious heat signs. Sows that are afflicted by a particular condition, such as leg problem, serious leanness, or by any other important health problem that affects the natural behavior of the sow, can negatively affect the accuracy of insemination requests, and therefore should be the object of particular attention.

The system sensibly reduces the workload of gestation swine barn workers by eliminating most of traditional systematic heat detection, and by reducing the number of inseminations. The system determines the best moment to inseminate sows during their heat cycle, which occurs most of the time when the natural stress of the sow is at its lowest point, which means early morning or late evening. Satisfying insemination request in a timely manner when prompted, allows the worker to increase gestation results and the prolificacy of the herd as a whole.

Below are the equations used to get the control parameters used by the algorithm for every GIT.

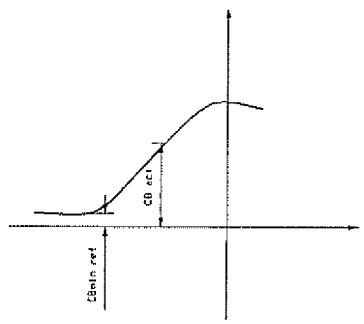
$$\%CB\min = \frac{CBact - CBref}{CBref} * 100$$
$$\%CBDelta = (CBact - CBref) * 100$$
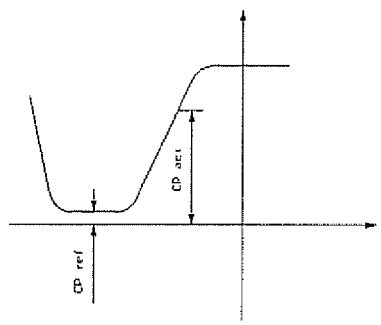
$$\%CPprev = \frac{CPact - CP.ref}{CP.ref} * 100$$
$$\%CPDelta = (CPact - CP.ref) * 100$$

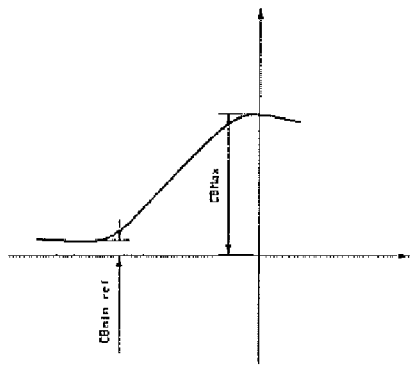
$$CBMPV = (CB\max - CBref)$$

The invention claimed is:

1. A method for monitoring estrus and ovulation of an animal for insemination comprising:
   detecting using a sensing system a changing characteristic of the animal indicative of estrus and ovulation of the animal;
   collecting data from the sensing system;
   using a processor to analyze the collected data using an algorithm to determine a time period of estrus and a time period of ovulation of the animal and a preferred time of insemination within the time period of ovulation;
   indicating on an indicating system to a worker the preferred time of insemination within the time period of ovulation;
   requiring the worker to enter an input indicative of an actual time of insemination;
   and, in the event that the insemination fails to cause fertilization, indicating on the indicating system whether the actual time of insemination entered by the worker occurred at the preferred time of insemination indicated to the worker;
   wherein the collection of the collected data is commenced on the animal when there is an expectation that the animal will enter estrus;
   wherein, subsequent to the commencement, within each of a plurality of time periods for each day, time data is determined relating to the total time during which the animal is standing within the time period;
   and wherein the processor is configured to analyze the time data using the algorithm to compare the time data relative to an average calculated from previous periods since the commencement.

2. The method according to claim 1 wherein the algorithm is arranged to calculate, from comparing the time data with the average, a start time of the changes.

3. The method according to claim 2 wherein the algorithm is arranged to calculate the start time of estrus by interpolation of the time data to work back from the time that the changes are detected to the actual start time of those changes.

4. The method according to claim 2 wherein the algorithm is arranged to calculate the start time by providing a moving integration of the time data and calculating two moving averages, one fast and the other slow, of the moving integral where a positive difference between the fast moving average and the slow moving average is used to determine the beginning of the estrus.

5. The method according to claim 1 wherein the algorithm is arranged to calculate, from comparing the time data with the average, a peak in the changes.

6. A method for monitoring estrus and ovulation of an animal for insemination comprising:
   detecting using a sensing system a changing characteristic of the animal indicative of estrus and ovulation of the animal;
   collecting data from the sensing system;
   using a processor to analyze the collected data using an algorithm to determine a time period of estrus and a time period of ovulation of the animal and a preferred time of insemination within the time period of ovulation;
   indicating on an indicating system to a worker the preferred time of insemination within the time period of ovulation;
   requiring the worker to enter an input indicative of an actual time of insemination;
   and when estrus is completed, the algorithm is used to provide a calculation of a confidence level regarding fertilization based on the actual time of insemination entered by the worker relative to the time period of ovulation;
   wherein the collection of the collected data is commenced on the animal when there is an expectation that the animal will enter estrus;
   wherein, subsequent to the commencement, within each of a plurality of time periods for each day, time data is determined relating to the total time during which the animal is standing within the time period;
   and wherein the processor is configured to analyze the time data using the algorithm to compare the time data relative to an average calculated from previous periods since the commencement.

7. The method according to claim 6 wherein the algorithm is arranged to calculate, from comparing the time data with the average, a start time of the changes.

8. The method according to claim 7 wherein the algorithm is arranged to calculate the start time of estrus by interpolation of the time data to work back from the time that the changes are detected to the actual start time of those changes.

9. The method according to claim 7 wherein the algorithm is arranged to calculate the start time by providing a moving integration of the time data and calculating two moving averages, one fast and the other slow, of the moving integral where a positive difference between the fast moving average and the slow moving average is used to determine the beginning of the estrus.

10. The method according to claim 6 wherein the algorithm is arranged to calculate, from comparing the time data with the average, a peak in the changes.

11. A method for monitoring estrus and ovulation of an animal for insemination comprising:
    detecting using a sensing system a changing characteristic of the animal indicative of estrus and ovulation of the animal;
    collecting data from the sensing system;
    using a processor to analyze the collected data using an algorithm to determine a time period of estrus and a time period of ovulation of the animal and a preferred time of insemination within the time period of ovulation;
    indicating on an indicating system to a worker the preferred time of insemination within the time period of ovulation;
    wherein, in the event that the preferred time of insemination within the ovulation time period is outside a scheduled work period, communicating to the worker an alternative time of insemination within a scheduled work period;
    wherein the collection of the collected data is commenced on the animal when there is an expectation that the animal will enter estrus;
    wherein, subsequent to the commencement, within each of a plurality of time periods for each day, time data is determined relating to the total time during which the animal is standing within the time period;
    and wherein the processor is configured to analyze the time data using the algorithm to compare the time data relative to an average calculated from previous periods since the commencement.

12. The method according to claim 11 wherein the algorithm is arranged to calculate, from comparing the time data with the average, a start time of the changes.

13. The method according to claim 12 wherein the algorithm is arranged to calculate the start time of estrus by interpolation of the time data to work back from the time that the changes are detected to the actual start time of those changes.

14. The method according to claim 12 wherein the algorithm is arranged to calculate the start time by providing a moving integration of the time data and calculating two moving averages, one fast and the other slow, of the moving integral where a positive difference between the fast moving average and the slow moving average is used to determine the beginning of the estrus.

15. The method according to claim 11 wherein the algorithm is arranged to calculate, from comparing the time data with the average, a peak in the changes.

16. A method for monitoring estrus and ovulation of an animal for insemination comprising:
    detecting using a sensing system a changing characteristic of the animal indicative of estrus and ovulation of the animal;
    collecting data from the sensing system;
    using a processor to analyze the collected data using an algorithm to determine a time period of estrus and a time period of ovulation of the animal and a preferred time of insemination within the time period of ovulation;
    indicating on an indicating system to a worker the preferred time of insemination within the time period of ovulation;
    wherein, in the event that the preferred of insemination within the ovulation time period is beyond the end of a first scheduled work period and before the beginning of a second scheduled work period, the processor makes a first determination whether insemination before the end of the first scheduled work period is desirable and makes a second determination as to whether an additional second insemination after the start of the second scheduled work period is desirable;
    and wherein the indicating system provides an indication to the worker of the results of the first and second determinations.

17. The method according to claim 16 wherein the indicating system is arranged to communicate to the worker two alternative times of insemination, one before the end of the first scheduled period and the second at the beginning of the second scheduled period.

18. The method according to claim 16 wherein the collection of the collected data is commenced on the animal when there is an expectation that the animal will enter estrus;
    wherein, subsequent to the commencement, within each of a plurality of time periods for each day, time data is determined relating to the total time during which the animal is standing within the time period;
    and wherein the processor is configured to analyze the time data using the algorithm to compare the time data relative to an average calculated from previous periods since the commencement.

19. The method according to claim 18 wherein the algorithm is arranged to calculate, from comparing the time data with the average, a start time of the changes.

20. The method according to claim 19 wherein the algorithm is arranged to calculate the start time of estrus by interpolation of the time data to work back from the time that the changes are detected to the actual start time of those changes.

21. The method according to claim 18 wherein the algorithm is arranged to calculate the start time by providing a moving integration of the time data and calculating two moving averages, one fast and the other slow, of the moving integral where a positive difference between the fast moving average and the slow moving average is used to determine the beginning of the estrus.

22. The method according to claim 18 wherein the algorithm is arranged to calculate, from comparing the time data with the average, a peak in the changes.

* * * * *